United States Patent [19]

Closs et al.

[11] Patent Number: 5,429,770
[45] Date of Patent: Jul. 4, 1995

[54] LOW-MOLECULAR-WEIGHT AND POLYMERIC LIQUID-CRYSTALLINE BENZOTRIAZOLES, AND THE USE THEREOF

[75] Inventors: Friedrich Closs; Karl Siemensmeyer, both of Frankenthal; Dirk Funhoff, Heidelberg, all of Germany

[73] Assignee: BASF Aktiengesellschaft, Ludwigshafen, Germany

[21] Appl. No.: 245,550

[22] Filed: May 18, 1994

[30] Foreign Application Priority Data

May 21, 1993 [DE] Germany .................. 43 17 093.5

[51] Int. Cl.[6] .................. C09K 19/34; C09K 19/38; G03G 5/06; C07D 403/00
[52] U.S. Cl. .................. 252/299.61; 430/76; 430/78; 544/359; 548/257; 548/259; 252/299.62
[58] Field of Search .................. 252/299.01, 299.61, 252/299.62; 430/56, 58, 76, 78; 548/255, 257, 259; 544/358, 359

[56] References Cited

U.S. PATENT DOCUMENTS

| | | | |
|---|---|---|---|
| 3,871,882 | 5/1975 | Wiedemann | 96/1.5 |
| 4,419,427 | 12/1983 | Graser et al. | 430/58 |
| 4,533,612 | 8/1985 | Eilingsfeld et al. | 430/59 |
| 4,710,446 | 12/1987 | Hoffmann et al. | 430/281 |
| 4,716,234 | 12/1987 | Dunks et al. | 548/259 |
| 5,132,429 | 7/1992 | Narita et al. | 548/257 |

FOREIGN PATENT DOCUMENTS 93330 11/1983 European Pat. Off. .

OTHER PUBLICATIONS

Houben–Weyl "Methoden Der Organischen Chemie", 4. Ed. vol. X13, p. 425 ff.

Primary Examiner—Shean Wu
Attorney, Agent, or Firm—Keil & Weinkauf

[57] ABSTRACT

Low-molecular-weight and polymeric liquid-crystalline 2-substituted benzotriazoles of the formula

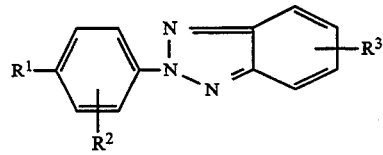

are used as photoconductors or electrophotographic recording materials or as fluorescent dyes for fluorescent displays.

3 Claims, No Drawings

LOW-MOLECULAR-WEIGHT AND POLYMERIC LIQUID-CRYSTALLINE BENZOTRIAZOLES, AND THE USE THEREOF

BACKGROUND OF THE INVENTION

1. Field of the Invention

The present invention relates to low-molecular-weight and polymeric liquid-crystalline 2-substituted benzotriazoles, to the use thereof as photoconductors (compounds which transport charge carriers) in electrophotographic recording materials, and to the use thereof for fluorescent displays on the basis of the strong fluorescence of these liquid crystals.

Photoconductors are widely employed in industry in copiers, laser printers and offset printing plates.

2. Description of the Prior Art

EP-A 93 329 and EP-A 93 330 disclose electrophotographic recording materials which contain, as photoconductor, triazoles of the formula

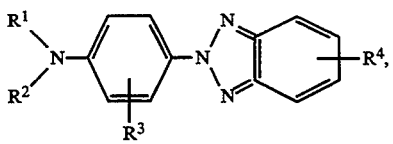

where $R^1$ and $R^2$ are, inter alia, oxygen, alkyl, allyl, benzyl or substituted or unsubstituted phenyl, $R^3$ is hydrogen, alkyl, alkoxy or halogen and $R^4$ is hydrogen, alkyl, alkoxy, vinyl, allyl, dialkylamino, nitro, cyano or acryloyl.

A disadvantage of the benzotriazoles used hitherto is their great tendency towards crystallization in most binder systems. Photoconductor layers are therefore frequently produced using complex mixtures of photoconductors.

A general disadvantage of organic photoconductors is their low charge carrier mobility. For use in fast laser printers or copiers, it has therefore hitherto been necessary to fall back on inorganic photoconductors, which contain toxic selenium.

On the other hand, it is known that highly ordered systems, such as monocrystalline anthracene, have higher charge carrier mobilities. There has therefore been no lack of attempts to utilize the liquid-crystalline order in low-molecular-weight or polymeric liquid crystals to produce faster photoconductors. Evidence has recently been found of increased photoconduction in the diskotic phase (cf. DE-A 41 26 496) and the nematic phase (cf. DE-A-42 11 087).

It is an object of the present invention to provide benzotriazoles having liquid-crystalline properties, in particular those which are photoconductive and have higher photoconductivity in the liquid-crystalline phase and in the non-liquid-crystalline phase. In addition, it is of interest whether the strong fluorescence of 2-aminophenylbenzotriazoles is also retained in the liquid-crystalline representatives.

SUMMARY OF THE INVENTION

We have found, surprisingly, that this object is achieved by certain 2-substituted benzotriazoles, which have a liquid-crystalline behavior. In spite of deviating from the ideal linear rod shape, the benzotriazoles have nematic and smectic phases, in some cases with a large phase range. In addition, some representatives are good photoconductors and exhibit higher photoconductivity in the liquid-crystalline phase than in the isotropic or polycrystalline phase. Furthermore, the novel benzotriazoles are distinguished by high fluorescence.

DESCRIPTION OF THE PREFERRED EMBODIMENTS

The present invention accordingly provides liquid-crystalline 2-substituted benzotriazoles of the formula (I)

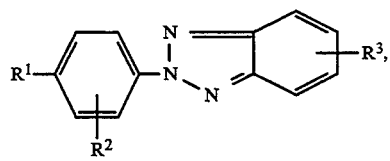

where
$R^1$ is $NR^4R^5$ or

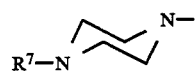

where
$R^4$ is H or $C_1$–$C_{12}$-alkyl,
$R^5$ is $C_5$–$C_{12}$-alkyl and
$R^7$ is $C_5$–$C_{12}$-alkyl, $C_5$–$C_{12}$-acyl, vinyl, $C_3$–$C_6$-alkenyl, acryloyl or methacryloyl,
$R^2$ is H, $C_1$–$C_{12}$-alkyl, $C_1$–$C_{12}$-alkoxy, hydroxyl or halogen, and
$R^3$ is

where X is O or S, a is 0 or 1, b is 0, 1 or 2, and c is 0 or 1, but where a and b must not simultaneously be 0 and where Y is $C_2$–$C_{11}$-alkylene or oxaalkylene having 1 to 5 oxygen atoms and 3 to 12 carbon atoms, and $R^6$ is —$CH_3$, —$OCH_3$, —$CH=CH_2$, —$O$—$CH=CH_2$,

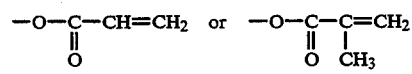

with the proviso that, in the case where
$R^1$ is

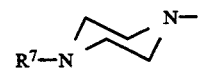

$R^3$ is H, $C_1$–$C_{12}$-alkoxy, $C_1$–$C_{12}$-acyloxy, nitro, cyano, dialkylamino, acryloyl or methacryloyl.

The present invention also provides polymeric benzotriazoles having a degree of polymerization of from 2 to 100, prepared from monomeric units of the formula (II)

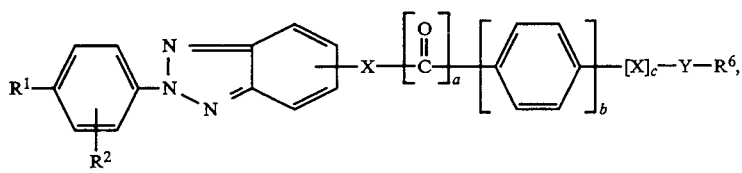

where $R^1$, $R^2$, X, Y, a, b and c are as defined in claim 1, and $R^6$ is a polymerizable radical from the group consisting of —CH=CH$_2$, —O—CH=CH$_2$,

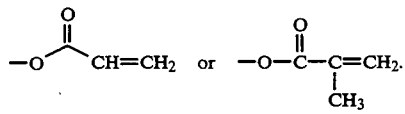

The present invention also provides electrophotographic recording materials comprising an electroconductive layer support, a charge carrier-producing sensitizer layer and a photoconductive layer, where the photoconductive layer contains one or more low-molecular-weight or polymeric 2-substituted benzotriazoles of the formula (I) or (II).

The present invention also provides the use of the liquid-crystalline 2-substituted benzotriazoles for fluorescent displays.

The increase in the photoconductivity in the novel benzotriazoles having calamitic properties can also be achieved by a homogeneously planar alignment of the charge-carrier molecules, which can be aligned by mechanical shearing or stretching, by applying an electrical or magnetic field, or by thermal treatment.

Novel low-molecular-weight liquid-crystalline 2-substituted benzotriazoles are those of the formula (I)

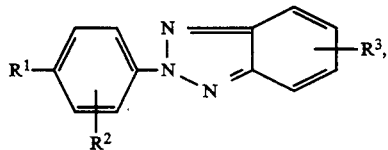

where
$R^1$ is $NR^4R^5$ or

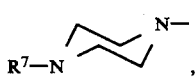

where
$R^4$ is H, $C_1$-$C_{12}$-alkyl, preferably $C_1$-$C_{15}$-alkyl, for example methyl, ethyl, propyl, butyl or pentyl and
$R^5$ is $C_5$-$C_{12}$-alkyl, preferably $C_6$-$C_{12}$-alkyl, for example hexyl or octyl,
$R^7$ is $C_5$-$C_{12}$-alkyl, preferably $C_5$-$C_8$-alkyl, for example pentyl, $C_5$-$C_{12}$-acyl, for example valeryl or capryl, vinyl, $C_3$-$C_6$-alkenyl, acryloyl or methacryloyl,
$R^2$ is H, $C_1$-$C_{12}$-alkyl, $C_1$-$C_{12}$-alkoxy, hydroxyl or halogen, for example F, Cl or Br, and
$R^3$ is

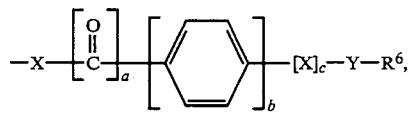

where X is O or S, a is 0 or 1, b is 0, 1 or 2, and c is 0 or 1, but where a, b and c must not simultaneously be 0, and where Y is $C_2$-$C_{11}$-alkylene or oxaalkylene having 1 to 5 oxygen atoms and 3 to 12 carbon atoms, and $R^6$ is —CH$_3$, —OCH$_3$, —CH=CH$_2$, —O—CH=CH$_2$,

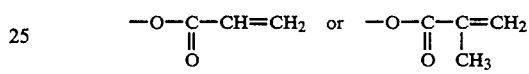

with the proviso that, in the case where $R^1$ is

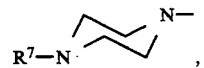

$R^3$ is H, $C_1$-$C_{12}$-alkoxy, for example methoxy, ethoxy, propoxy or butoxy, $C_1$-$C_{12}$-acyloxy, for example acetoxy, valeryl, capryl, nitro, cyano, dialkylamino, for example dimethylamino, diethylamino or dibutylamino, acryloyl or methacryloyl.

The novel 2-substituted benzotriazoles can be prepared by known methods of organic chemistry. For example, they can be obtained from ortho-nitroazo compounds of the formula (III)

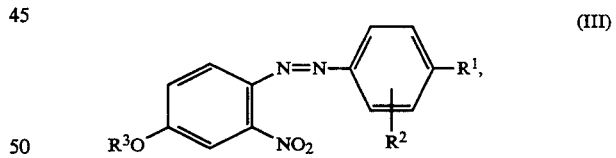

where $R^1$, $R^2$ and $R^3$ are as defined above, by the methods described in Houben-Weyl, Methoden der organischen Chemie, 4th Edition, Volume X/3, pp. 425 ff. Compounds of the formula (III) can be prepared by standard methods. Starting from 5-methoxybenzotriazoles, ether cleavage in hydrogen bromide-saturated water—as described in the examples—gives 5-hydroxybenzotriazoles.

Etherification by means of suitable alcohols or esterification by means of suitable acids or acid chlorides gives many such liquid-crystalline benzotriazoles in a simple manner by standard methods.

Novel polymeric liquid-crystalline benzotriazoles are those which contain a benzotriazole of the formula (I) bonded to a polymer chain via a flexible spacer.

The polymeric binding can be either at the hydroxyl group in the 5-position of the benzotriazole or at the terminal nitrogen of the 2-aminophenyl or 2-pyrazinylphenyl radical. Standard methods starting from the corresponding monomer precursors give polyacrylates, polymethacrylates, polysiloxanes and polyvinyl ethers. An example of a polymeric liquid-crystalline benzotriazole is

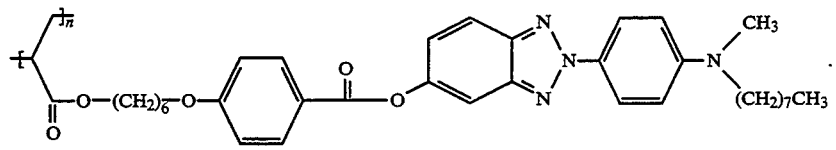

For the use of the novel liquid-crystalline 2-substituted benzotriazoles for electrophotographic recording materials, sensitizers, ie. charge carrier-producing compounds, can be added in order to increase the photosensitivity of the layers. Examples of compounds of this type are the perylenetetracarboxylic acid derivatives disclosed in DE-A 22 37 399 and DE-A 31 10 955. Particular preference is given to sensitizers such as Rhodamine B (C.I. 45170) and Astrazone Orange (C.I. 48035).

The novel photoconductors are generally used in the form of thin photoconductive layers, it also being possible to separate the charge transport from the charge production by means of a two-layer arrangement, as used in electrophotography. In this case, the novel photoconductor is in the photoconductive charge-transport layer, which is adjacent to a conventional and known charge carrier-producing sensitizer layer. The charging here is generally effected by a high-voltage corona.

The production of the novel layers on a support surface can be carried out by application of a melt or in a conventional and known manner, for example by knife coating a solution of the compounds onto a support surface. In this case, various auxiliaries, for example for improving the flow properties, can be added to the solution.

Examples of solvents which can be used are tetrahydrofuran and dichloromethane.

These photoconductive layers generally have a thickness of from 1 to 100 μm, preferably from 1 to 50 μm, particularly preferably from 1 to 30 μm.

The photoconductors or photoconductive layers can be arranged between conductively coated, transparent substrates, for which glass plates or plates of optically transparent plastics (for example polymethyl methacrylate, polycarbonate, etc.) are used. The conductive coating of the substrate can comprise electroconductive polymers, semiconductors or metals, for example aluminum, silver or gold. However, the thickness of the coating should be selected so that the optical transparency is not impaired excessively. Particularly advantageous coatings comprise ITO (indium tin oxide).

In order to generate a photocurrent, a direct voltage of from 5 to 50 V is generally applied to the electroconductively coated plates.

The liquid-crystalline calamitic state, in which the photoconductivity is higher than in the unordered, isotropic state, can advantageously be produced by a homogeneously planar alignment. The alignment of the charge carriers can be achieved, for example, mechanically (by stretching or shearing) or by electric or magnetic fields. Alignment can also be produced by means of orienting sublayers containing or comprising, for example, polyimides. The simplest method is thermal treatment (conditioning).

The novel photoconductors and photoconductive films can be used in electrophotography, in laser printers, in offset printing, or alternatively in microelectronics for photosensitive switches. In addition, the invention can be employed in all areas where the increase in photoconductivity by molecular order is utilized.

The invention is described by means of the examples which follow.

In the examples, parts and percentages are by weight, unless specified otherwise.

In the phase behavior data,
c denotes the crystalline phase,
$S_A$ denotes the smectic A phase,
n denotes the nematic phase,
LC denotes an unidentified liquid-crystalline phase, and
i denotes the isotropic melt.

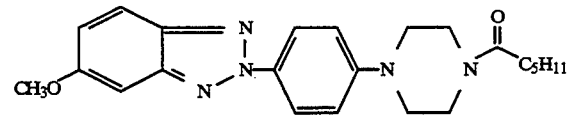

36 g of 4-methoxy-2-nitro-4'N-caproylpyrazinylazobenzene and 97 g of triethyl phosphite were refluxed for 4 hours, the mixture was cooled and filtered with suction, and the product was recrystallized from methanol, giving 23 g of yellow crystals.

Phase behavior: c 197.9° C. $S_A$ 201.7° C. i
$C_{23}H_{29}N_5O_2$
Analysis:

|  | C | H | N | O |
|---|---|---|---|---|
| calc. | 67.8 | 7.2 | 7.9 | 17.2 |
| found | 67.8 | 7.3 | 8.1 | 17.4 |

EXAMPLE 2

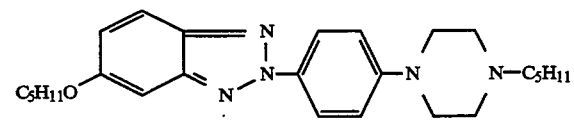

a) 20 g of 5-methoxy-2-(4-caproylpyrazinylphenyl)-benzotriazole (Ex. 1) were heated for 6 hours at 120° C. with 112 g of 47% strength HBr in water. The colorless solid was filtered off with suction, washed with water until neutral and dried at 40° C. under reduced pressure.

Crude yield: 19 g of 5-hydroxy-2- (4-pyrazinylphenyl)benzotriazole hydrobromide.

b) 17 g of the hydrobromide were refluxed for 6 hours with 24.4 g of pentyl bromide, 6 g of KOH and 118 g of EtOH/5 g of H₂O. The batch was poured into 100 g of H₂O, and the solid was filtered off with suction and dried at 50° C. under reduced pressure, giving 19.8 g of yellow crystals (recrystallized from ethyl acetate).

Phase behavior: c 102° C. S$_A$ 151° C. i C$_{26}$H$_{37}$N$_5$O

Analysis:

|   | C | H | N | O |
|---|---|---|---|---|
| calc. | 71.7 | 8.6 | 16.1 | 3.7 |
| found | 71.5 | 8.7 | 15.7 | 3.9 |

EXAMPLE 3

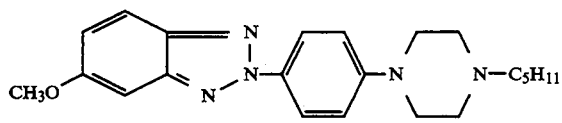

1.3 g of 4-methoxy-2-nitro-4'N-pentylpyrazinylazobenzene and 19 g of triethylphosphite were refluxed for 3 hours, and the mixture was cooled, giving 0.5 g of yellow crystals.

Phase behavior: c 113° C. S$_A$ 190.8° C. n 191.7° C. i

C$_{22}$H$_{29}$N$_5$O

Analysis:

|   | C | H | N | O |
|---|---|---|---|---|
| calc. | 69.6 | 7.7 | 18.5 | 4.2 |
| found | 69.4 | 7.8 | 18.3 | 4.5 |

EXAMPLE 4

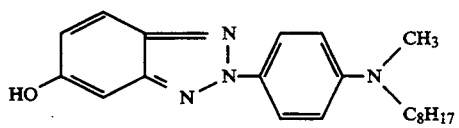

40 g of 5-methoxy-2-[4-(methyl-n-octylamino)phenyl]benzotriazole were refluxed for 6 hours with 440 g of 47% strength HBr in H₂O, the mixture was cooled and filtered with suction, and the solid was washed with water until neutral and dried at 50° C. under reduced pressure.

Yield: 40.5 g of 5-hydroxy-2-[4-(methyl-n-octylamino)phenyl]benzotriazole hydrobromide.

EXAMPLE 5

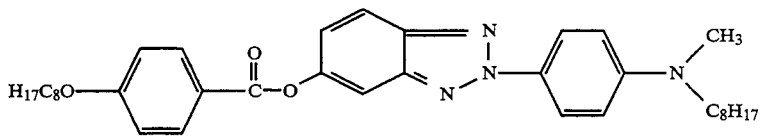

8.7 g of 5-hydroxy-2-[4-(methyl-n-octylamino)phenyl]benzotriazole hydrobromide and 8.6 g of 4-octyloxybenzoyl chloride were refluxed for 5 hours in 29 g of pyridine. The batch was cooled to room temperature, filtered and poured into 100 g of dilute HCl. The yellow crystals were filtered off with suction.

Yield: 7 g of C$_{36}$H$_{48}$N$_4$O$_3$

Phase behavior: monotropic liquid crystal

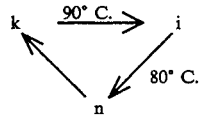

EXAMPLE 6

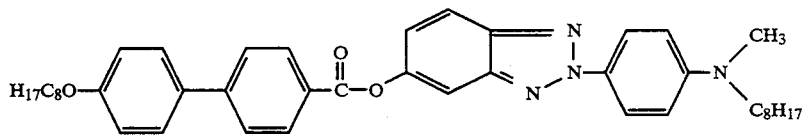

2.4 g of 4-octyloxy-4'-chlorocarbonylbiphenyl and 4.3 g of 5-hydroxy-2-[4-(methyl-n-octylamino)phenyl]benzotriazole hydrobromide were refluxed for 6 hours in 40 g of pyridine. The batch was cooled and poured into 200 g of dilute HCl. The pale yellow crystals were filtered off with suction and washed with water.

Yield: 3 g (recrystallized from ethyl acetate) of C$_{36}$H$_{48}$N$_4$O$_3$

Phase behavior: c 181° C. n 228.4° C. i

EXAMPLE 7

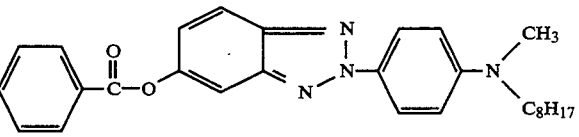

5.6 g of 5-hydroxy-2-[4-(methyl-n-octylamino)phenyl]benzotriazole hydrobromide, 5.0 g of 4-acryloyloxyhexoxybenzoic acid and 0.3 g of 4-pyrrolidinopyridine were dissolved in 250 g of dry methylene chloride. 6 g of dicyclohexylcarbodiimide in 125 g of dry methylene chloride were added dropwise at from 0° to +5° C. The mixture was then stirred at room temperature for 18 hours, and the insoluble residue was separated off. The solvent was evaporated under reduced pressure, and the residue was recrystallized from ethanol.

Yield: 7 g of $C_{37}H_{46}N_4O_5$

Polymerization takes place in the region of the melting point (80° C.).

EXAMPLE 8

3.8 g of the monomer from Example 7 were dissolved in 88 g of dry THF. 0.4 g of Porofor N was added, and the mixture was flushed with argon, stirred at 50° C. for 100 hours and filtered. Methanol was added to the filtrate, depositing the polymer as an oil, which was reprecipitated a number of times from THF/methanol.

Yield: 3.3 g DSC: g 48° C. n 65° C. i (DSC=differential thermoanalysis; g=glass phase) Degree of polymerization: 5–6 (according to GPC=Gel Permeation Chromatography)

EXAMPLE 9

Photoconduction in the liquid-crystalline phase of liquid-crystalline benzotriazole derivatives In order to determine the photocurrent in the liquid-crystalline phase, a 1:1 mixture of the substances from Examples 5 and 6 was prepared by melting them with one another. The phase transition temperatures of this mixture were:

c 60° C. LC 145° C. i.

The mixture to be investigated was prepared in a measurement cell comprising two glass plates with a transparent, conductive coating of indium tin oxide. The coating thickness of the sample was about 10 μm, set by means of an 8 μm polyester film. The electrode area was 4 mm². A direct voltage signal of 9 V, corresponding to an applied field strength of about 900 kV m$^{-1}$, was applied to the sample. The sample was illuminated by means of a cold light source. The incident light beam was modulated by means of a chopper with a frequency of 10 Hz, ie. was chopped into light pulses with a length of 50 msec with a dark phase of the same length. The photocurrent was detected by means of the voltage drop over a 182,000 Ω resistance by means of a lock-in amplifier (EG&G 5210). In order to be able to study the temperature dependence of the sample, it was conditioned on a heating stage (Mettler FP 80/82).

The following values were obtained from the above mixture:

| Temperature [°C.] | Photocurrent [pA] | Phase |
| --- | --- | --- |
| 40 | 5 | crystalline |
| 70 | 15 | liquid-crystalline |
| 100 | 50 | liquid-crystalline |
| 110 | 70 | liquid-crystalline |
| 130 | 130 | liquid-crystalline |
| 150 | 65 | isotropic |

As is evident from the table, the sample exhibited virtually no photocurrent in the crystalline phase. This increased greatly in the liquid-crystalline phase, and then dropped again in the isotropic phase.

We claim:

1. A 2-substituted benzotriazole of the formula (I)

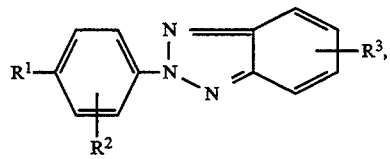

where
$R^1$ is $NR^4R^5$ or

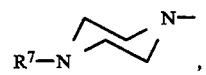

where
$R^4$ is H or $C_1-C_{12}$-alkyl,
$R^5$ is $C_5-C_{12}$-alkyl and
$R^7$ is $C_5-C_{12}$-alkyl, $C_5-C_{12}$-acyl, vinyl, $C_3-C_6$-alkenyl, acryloyl or methacryloyl,
$R^2$ is H, $C_1-C_{12}$-alkyl, $C_1-C_{12}$-alkoxy, hydroxyl or halogen, and
$R^3$ is

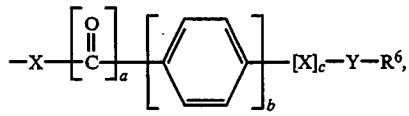

where X is O or S, a is 0 or 1, b is 0, 1 or 2, and c is 0 or 1, but where a and b must not simultaneously be 0 and where Y is $C_2-C_{11}$-alkylene or oxaalkylene having 1 to 5 oxygen atoms and 3 to 12 carbon atoms, and $R^6$ is $-CH_3$, $-OCH_3$, $-CH=CH_2$, $-O-CH=CH_2$,

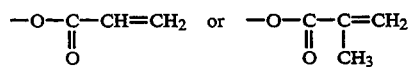

with the proviso that, in the case where $R^1$ is

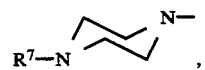

$R^3$ is H, $C_1-C_{12}$-alkoxy, $C_1-C_{12}$-acyloxy, nitro, cyano, dialkylamino, acryloyl or methacryloyl.

2. A liquid-crystalline, polymeric benzotriazole having a degree of polymerization of from 2 to 100, prepared from monomeric units of the formula (II)

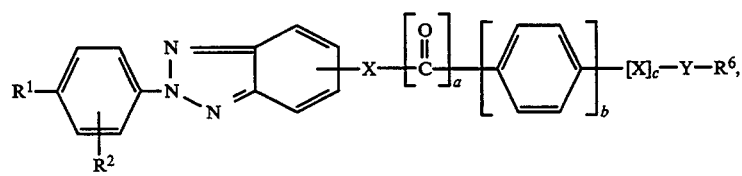

where R¹, R², X, Y, a, b and c are as defined in claim 1, and R⁶ is a polymerizable radical from the group consisting of —CH=CH₂, —O—CH=CH₂,

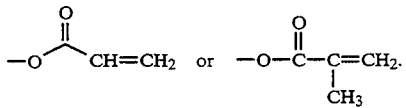

3. An electrophotographic recording material comprising an electroconductive layer support, a charge carrier-producing sensitizer layer and a photoconductive layer, where the photoconductive layer contains one or more 2-substituted benzotriazoles as defined in claim 1.

* * * * *